United States Patent
Ecoff et al.

(10) Patent No.: US 9,226,702 B2
(45) Date of Patent: Jan. 5, 2016

(54) COMMUNICATION PROTOCOL IMPROVEMENT TO RECOVER DATA FROM A CONTINUOUS GLUCOSE MONITOR

(71) Applicant: Roche Diagnostics Operations, Inc., Indianapolis, IN (US)

(72) Inventors: Clint A. Ecoff, Indianapolis, IN (US); Sheldon A. White, Westfield, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 700 days.

(21) Appl. No.: 13/650,160

(22) Filed: Oct. 12, 2012

(65) Prior Publication Data

US 2014/0107449 A1     Apr. 17, 2014

(51) Int. Cl.
| | |
|---|---|
| G08B 1/08 | (2006.01) |
| A61M 1/00 | (2006.01) |
| A61B 5/00 | (2006.01) |
| A61B 5/145 | (2006.01) |
| G06F 19/00 | (2011.01) |

(52) U.S. Cl.
CPC ........... *A61B 5/14532* (2013.01); *A61B 5/0015* (2013.01); *A61B 5/7232* (2013.01); *G06F 19/3418* (2013.01)

(58) Field of Classification Search
CPC ............. A61B 5/14532; A61B 5/0022; A61B 5/0026; G06F 19/3418
USPC ...................... 600/365; 340/539.12
See application file for complete search history.

(56) References Cited

U.S. PATENT DOCUMENTS

| | | | | |
|---|---|---|---|---|
| 5,745,268 | A | * | 4/1998 | Eastvold et al. ................ 398/25 |
| 6,436,052 | B1 | * | 8/2002 | Nikolic et al. ................ 600/529 |
| 7,261,691 | B1 | * | 8/2007 | Asomani ....................... 600/300 |
| 7,811,231 | B2 | | 10/2010 | Jin et al. |
| 8,123,686 | B2 | * | 2/2012 | Fennell et al. ................ 600/365 |
| 8,187,183 | B2 | | 5/2012 | Jin et al. |
| 2003/0007456 | A1 | * | 1/2003 | Gupta et al. .................. 370/232 |
| 2003/0107487 | A1 | * | 6/2003 | Korman et al. ............ 340/573.1 |
| 2003/0143973 | A1 | * | 7/2003 | Nagy et al. ..................... 455/403 |
| 2004/0034550 | A1 | * | 2/2004 | Menschik et al. ................ 705/3 |
| 2004/0186365 | A1 | | 9/2004 | Jin et al. |
| 2004/0249249 | A1 | * | 12/2004 | Lawson et al. ................ 600/300 |
| 2004/0267947 | A1 | * | 12/2004 | Sheahan et al. ............... 709/230 |
| 2005/0080322 | A1 | * | 4/2005 | Korman ......................... 600/300 |
| 2005/0197680 | A1 | * | 9/2005 | DelMain et al. ................ 607/60 |
| 2005/0281215 | A1 | * | 12/2005 | Budampati et al. ........... 370/328 |
| 2006/0036134 | A1 | * | 2/2006 | Tarassenko et al. .......... 600/300 |
| 2006/0189854 | A1 | * | 8/2006 | Webb et al. .................... 600/300 |
| 2007/0004971 | A1 | * | 1/2007 | Riley et al. .................... 600/300 |
| 2007/0010719 | A1 | * | 1/2007 | Huster et al. .................. 600/300 |
| 2007/0093974 | A1 | * | 4/2007 | Hoogenboom .................. 702/35 |
| 2008/0214900 | A1 | * | 9/2008 | Fennell et al. ................ 600/300 |
| 2008/0278333 | A1 | * | 11/2008 | Fennell et al. ............. 340/573.1 |

(Continued)

*Primary Examiner* — Fekadeselassie Girma
*Assistant Examiner* — Rufus Point
(74) *Attorney, Agent, or Firm* — Harness, Dickey (57) ABSTRACT

Data transmissions between medical devices are governed by various communication protocols. For example, blood glucose measures may be retrieved wirelessly from a continuous glucose monitor in accordance with the ANT wireless communication protocol. Smaller data packets are preferably transferred in a standard data transfer mode which is optimized for speed and power management; whereas, larger data packets are transferred in a file sharing mode. Techniques are presented to address recovering data lost during the standard data transfer mode in an efficient manner and preferably without the use of the file sharing mode.

21 Claims, 9 Drawing Sheets

(56) References Cited

U.S. PATENT DOCUMENTS

| | | | |
|---|---|---|---|
| 2008/0287761 A1* | 11/2008 | Hayter et al. | 600/365 |
| 2008/0309481 A1* | 12/2008 | Tanaka et al. | 340/539.12 |
| 2010/0014626 A1* | 1/2010 | Fennell et al. | 377/15 |
| 2011/0010534 A1* | 1/2011 | Lee et al. | 713/150 |
| 2011/0028817 A1 | 2/2011 | Jin et al. | |
| 2012/0255875 A1* | 10/2012 | Vicente et al. | 205/782 |
| 2013/0195091 A1* | 8/2013 | Gibbs et al. | 370/338 |
| 2014/0107449 A1* | 4/2014 | Ecoff et al. | 600/365 |

* cited by examiner

COMMUNICATION PROTOCOL IMPROVEMENT TO RECOVER DATA FROM A CONTINUOUS GLUCOSE MONITOR

FIELD

The present disclosure relates generally to continuous glucose monitors and more particularly to a communication protocol improvement for recovering data from a continuous glucose monitor.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated glucose levels that result from defects in the body's ability to produce and/or use insulin. There are three main types of diabetes. Type 1 diabetes can be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise and lifestyle. Lab test results include HbA1C, cholesterol, triglycerides, and glucose tolerance. Healthcare professional recommendations include prescriptions, diets, test plans, and other information relating to the patient's treatment.

In an example scenario, blood glucose levels may be measured on a continuous basis by a continuous glucose monitor and periodically transmitted from the continuous glucose monitor to another type of diabetes management device. During data transmission, an error may occur such that the blood glucose measures are lost or otherwise not received by the destination device. Communication protocols governing the data transmissions leave room for improvements to recover lost data in a more efficient manner from the continuous glucose monitor.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

According to the present disclosure, a communication protocol improvement is presented for recovering blood glucose measure sent from a continuous glucose monitor but not received by a diabetes management device.

In some embodiments, blood glucose measures are communicated wirelessly in accordance with the ANT wireless communication protocol. Smaller data packets are preferably transferred in a standard data transfer mode which is optimized for speed and power management; whereas, larger data packets are transferred in a file sharing mode. This disclosure addresses the problem of data lost during the standard data transfer mode and how to recover such data in an efficient manner and preferably without the use of the file sharing mode.

An improved method is presented for communicating data between a continuous glucose monitor and a handheld diabetes manager. The method includes: constructing a data packet for transmission during a current time interval in a series of sequential time intervals, where the data packet includes blood glucose measures taken by the continuous glucose monitor during the current time interval; resetting a counter upon receiving an acknowledgement of receipt of a data packet transmitted during the preceding time interval; incrementing the counter upon failing to receive an acknowledgement of receipt of a data packet transmitting during a time interval preceding the current time interval; appending blood glucose measures taken by the continuous glucose measure during the preceding time interval to the data packet when the counter is less than a threshold; transmitting the data packet at a first data rate via a wireless data link to the handheld diabetes manager when the counter is less than the threshold; storing blood glucose measures taken by the continuous glucose monitor during the current time interval and the preceding time interval in a non-volatile memory, when the counter is equal to or exceeds the threshold and upon failing to receive an acknowledgement of receipt of a data packet transmitting; and, subsequent to storing the blood glucose measures in the non-volatile memory, transmitting the blood glucose measures stored in the non-volatile memory at a second data rate higher than the first data rate.

In some embodiments, data packets are transmitted by the continuous glucose monitor in accordance with the ANT communication protocol.

In another example, the method includes: transmitting a first data packet via a wireless data link to the handheld data manager during a first time interval in a series of sequential time intervals, where the first data packet includes blood glucose measures taken by the continuous glucose monitor prior to the first time interval; receiving an acknowledgement regarding the transmission of the first data packet; retransmitting the first data packet via the wireless data link to the handheld data manager during the first time interval when the acknowledgement indicates an unsuccessful transmission of the first data packet; receiving an acknowledgement regarding the retransmission of the first data packet; and transmitting a second data packet via the wireless data link during a second time interval in the series of time intervals, wherein the second data packet includes blood glucose measures taken by the continuous glucose monitor during the first time interval and further includes blood glucose measures taken by the continuous glucose measure prior to the first time interval only when the acknowledgement indicates an unsuccessful retransmission of the first data packet.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Figure 1:
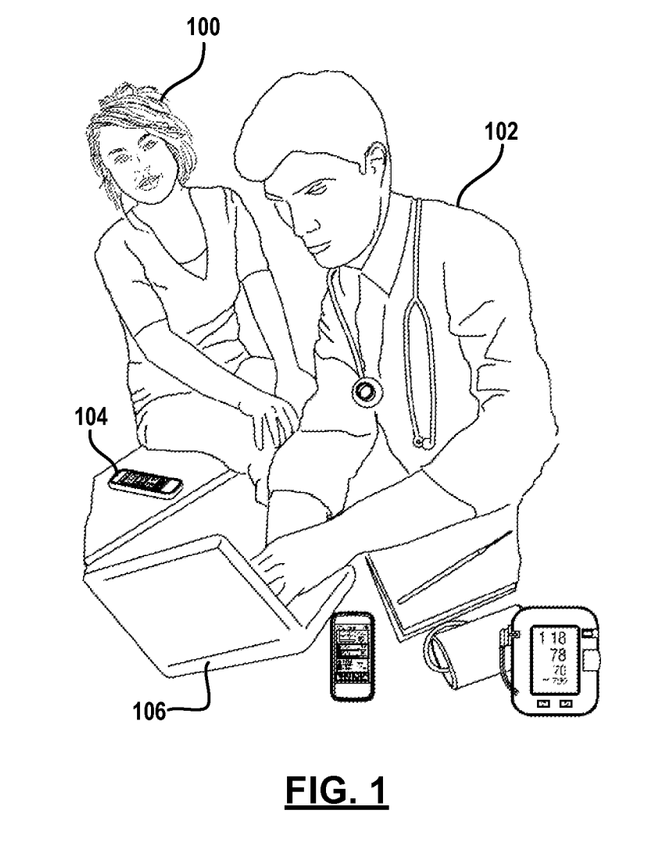
FIG. 1 shows a patient and a treating clinician.

FIG. 1 depicts a person 100 with diabetes and a healthcare professional 102 in a clinical environment. Persons with diabetes include persons with metabolic syndrome, pre-diabetes, type 1 diabetics, type 2 diabetics and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 can obtain additional patient data that includes measurements of HbA1C, cholesterol levels, triglycerides, blood pressure, and weight of the patient 100. The patient data can be recorded manually or electronically on a handheld diabetes managing device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100. In some instances, the patient data can be shared by the handheld managing device 104 via a wireless router with a computing device accessible to the clinician 102.

Figure 2:
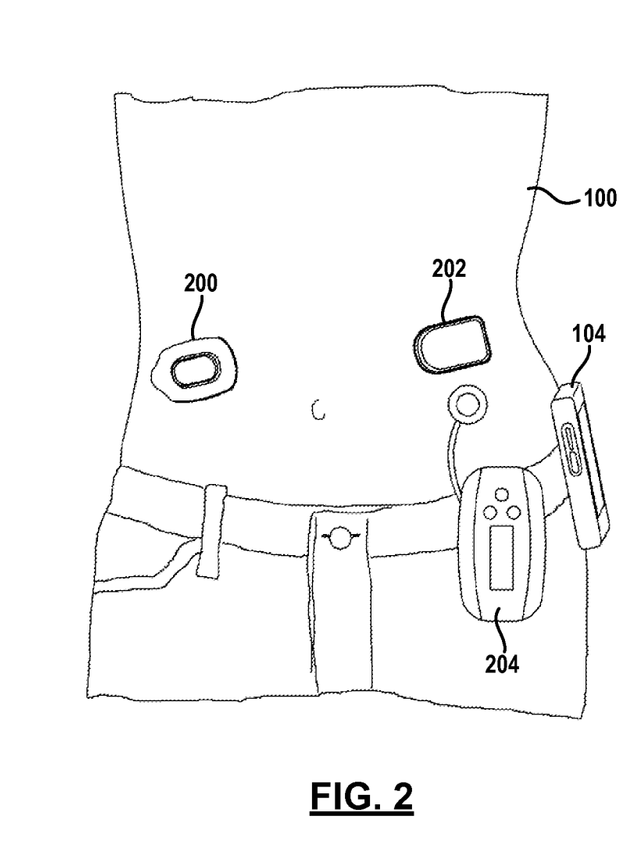
FIG. 2 shows a patient with a continuous glucose monitor (CGM), ambulatory durable insulin infusion pump, ambulatory non-durable insulin infusion pump, and diabetes manager.

The patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes managing device 104 (hereinafter the diabetes manager 104) as shown in FIG. 2. The CGM 200 uses a subcutaneous sensor to sense and monitor the amount of glucose in the subcutaneous fluid of the patient 100 and communicates corresponding readings to the handheld diabetes managing device 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating a glucose level in the subcutaneous fluid of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
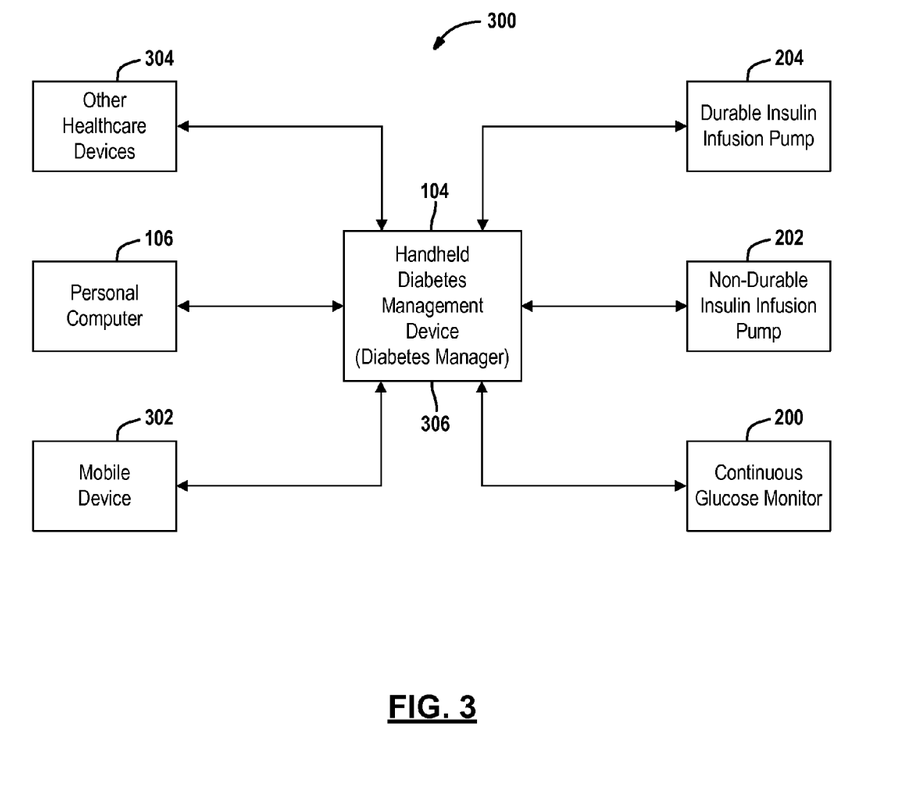
FIG. 3 shows a diabetes care system of systems used by patients and clinicians to manage diabetes.

FIG. 3 depicts an exemplary system 300 of devices used by the patient 100 and/or the clinician 102. Exemplary devices may include: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines.

The diabetes manager 104 can receive glucose readings from one or more sources (e.g., from the CGM 200). The CGM 200 continuously measures the glucose level of the patient 100. The CGM 200 periodically communicates the glucose level to the diabetes manager 104. In an exemplary embodiment, the diabetes manager 104 and the CGM 200 communicate wirelessly using ANT or ANT+ wireless communication protocol developed by Dynastream Innovations Inc. although other types of wireless communication protocols are contemplated by this disclosure.

The diabetes manager 104 may include a blood glucose meter (BGM) and a port that communicates with the BGM (both not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information for the devices of the diabetes management system 300. The configurator has a database to store configuration information for the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 can include a cellular phone, a PDA, or a pager. The diabetes manager 104 can send messages to an external network through the mobile device 302. The mobile device 302 can transmit messages to the external network based on requests received from the diabetes manager 104.

In some embodiments, the diabetes manager 104 can communicate with a wireless router (not shown) using Bluetooth, ANT+ or other wireless protocols. The wireless router is in turn interface with the PC 106 and/or another healthcare device 304. The wireless router can also be a standalone home-based portal located at the patient's residence or at the clinician's office.

In some embodiments, the CGM 200 measures the level of glucose in the interstitial fluid of the patient 100 by sampling a current. The level of glucose in the interstitial fluid, and therefore the sampled current, is related to the glucose level of the patient 100. In order to accurately estimate the glucose level of the patient 100 based on the interstitial fluid glucose level measured by the CGM 200, the diabetes manager 104 can be periodically calibrated.

The diabetes manager 104 can be calibrated by determining a calibration equation based on at least one current sample and at least one blood glucose measurement. The current sampled by the CGM 200 and the blood glucose level of the patient 100 can be assumed to have a linear relationship within a normal measurement region of approximately 40 to 400 Milligrams per Deciliter. Based on this assumed linear relationship, the calibration equation can be a linear equation that associates one or more current samples with an estimated glucose level of the patient. After calibration, the diabetes manager 104 can determine an estimated glucose level of the patient 100 based on the calibration equation and the current sampled by the CGM 200.

Figure 4:
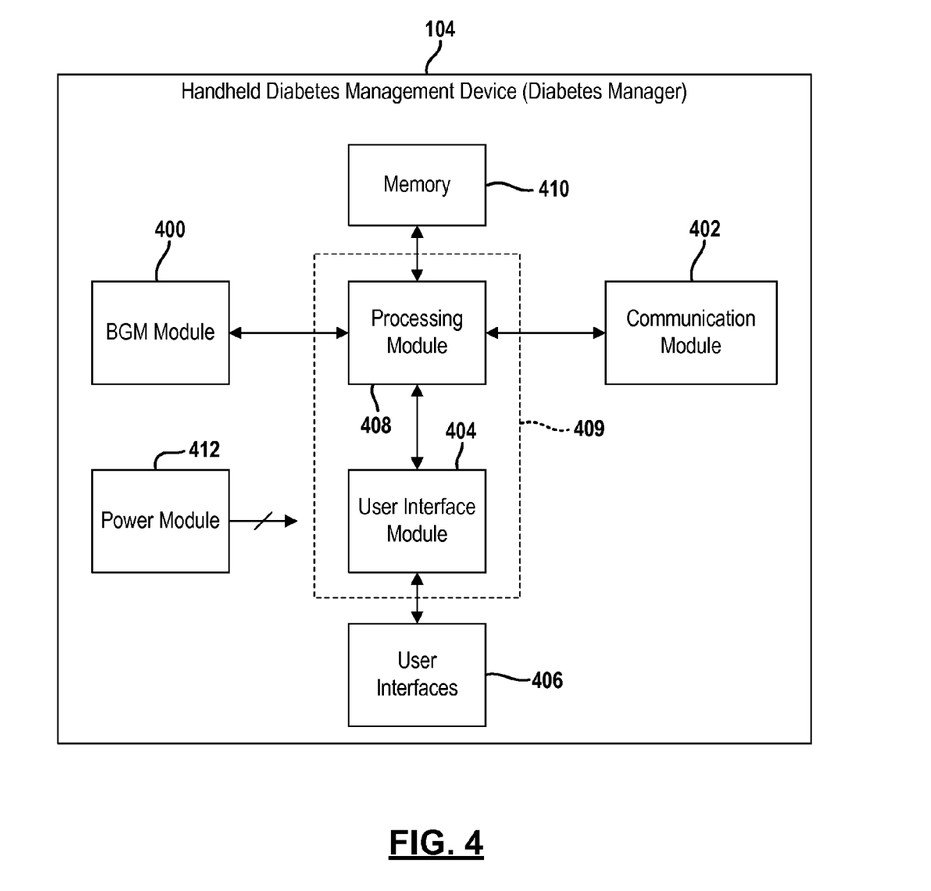
FIG. 4 is a functional block diagram of a diabetes manager.

With reference to FIG. 4, an exemplary diabetes manager 104 includes a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 can include multiple radios that communicate with different devices of the diabetes management system 300. The user interface module 404 connects the diabetes manager 104 to various user interfaces 406 that the patient 100 can use to interact with the diabetes manager 104. For example, the user interfaces 406 can include keys, switches, a display, a speaker, a microphone, a secure digital (SD) card port, and/or a USB port (all not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 can include a rechargeable battery or other source of power. The battery can be recharged, e.g., by using an adapter that plugs into a wall outlet and/or via a USB port on the diabetes manager 104.

Figure 5:
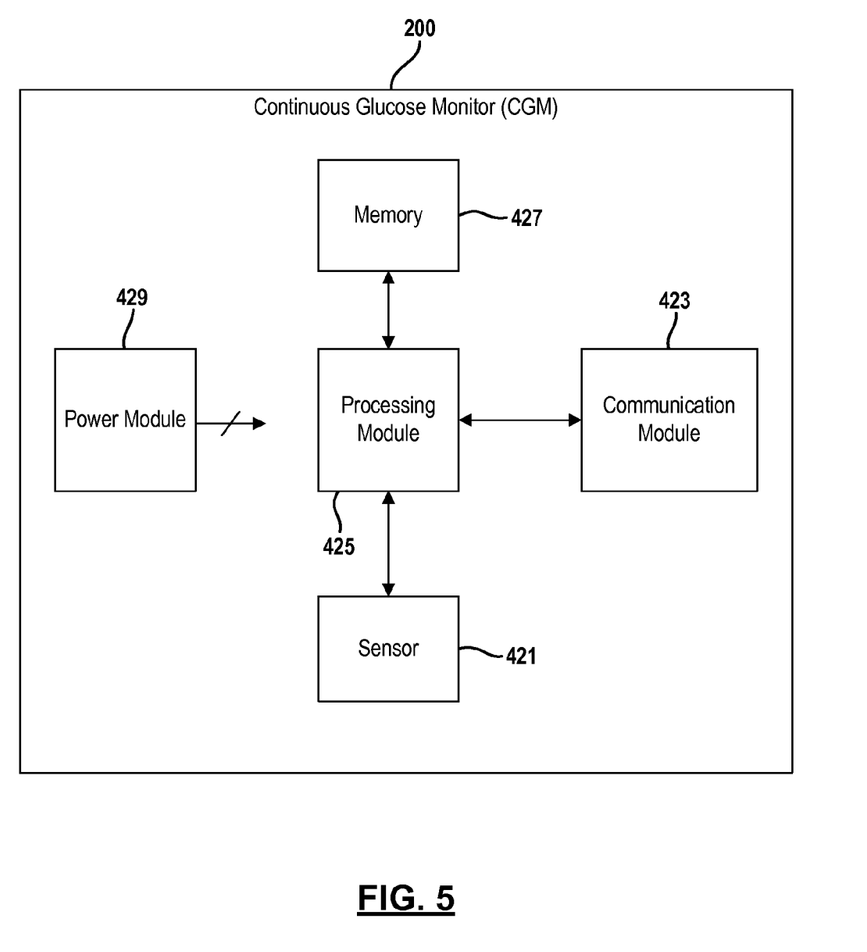
FIG. 5 is a functional block diagram of a continuous glucose monitor.

With reference to FIG. 5, an exemplary continuous glucose monitor (CGM) 200 includes a sensor 421, a communication module 423, a processing module 425, memory 427, and a power module 429. The sensor 421 can monitor a condition of the patient 100 that is related to the glucose level of the patient 100. For example, the sensor 421, alone or in combination with processing module 425, can periodically sample a current value that corresponds to the level of glucose in the interstitial fluid of the patient 100. The communication module 423 can include one or more radios that communicate with different devices of the diabetes management system 300.

The processing module 425 processes data received from the sensor 421 and the communication module 423. The processing module 425 uses memory 427 for processing and storing data. The memory 427 can include volatile and nonvolatile memory. The processing module 425 outputs data to and receives data from the devices (for example, diabetes manager 104) of the diabetes management system 300 via the communication module 423. The power module 429 supplies power to the components of the CGM 200. In some embodiments, the power module 429 includes a battery or other source of power. The source of power may include a battery that can be recharged, e.g., by using an adapter that plugs into a wall outlet.

In an exemplary embodiment, the CGM 200 communicates wirelessly with the diabetes manager 104 in accordance with the ANT and in particular ANT+ wireless communication protocol. ANT is a low-power wireless communication protocol operating in the 2.4 Gigahertz frequency band. An overview of this communication protocol is set forth below. Further details for ANT communication protocol and related protocols may be found at www.thisisant.com. While specific reference is made to the ANT communication protocol, it is envisioned that the concepts set forth below are extendable to other types of wireless communication protocols.

Devices communicating in accordance with ANT operate in two states: a beacon state and a data exchange state. The beacon state allows a slave device to transmit its presence to a master device. While in the beacon state, the slave device can broadcast a single beacon at a specified default beacon rate (e.g., once every five minutes). The beacon message contains transmission information, such as channel period and synchronization information. By default, the slave device operates in the beacon state. The slave device will transition to the data exchange state upon receipt of a valid request from the master device. Once in the data exchange state, the slave device can transmit data and other device status information to the master device. The slave device remains in the data exchange state until the expiration of a time period during which no messages were received from the master device or upon receipt of a request from the master device to return to the beacon state. In the context of this disclosure, the CGM 200 functions as the slave device and the diabetes manager 104 functions as the master device. It is readily understood that in other scenarios the CGM 200 functions as the master device and the diabetes manager 104 functions as the slave device.

Figure 6:
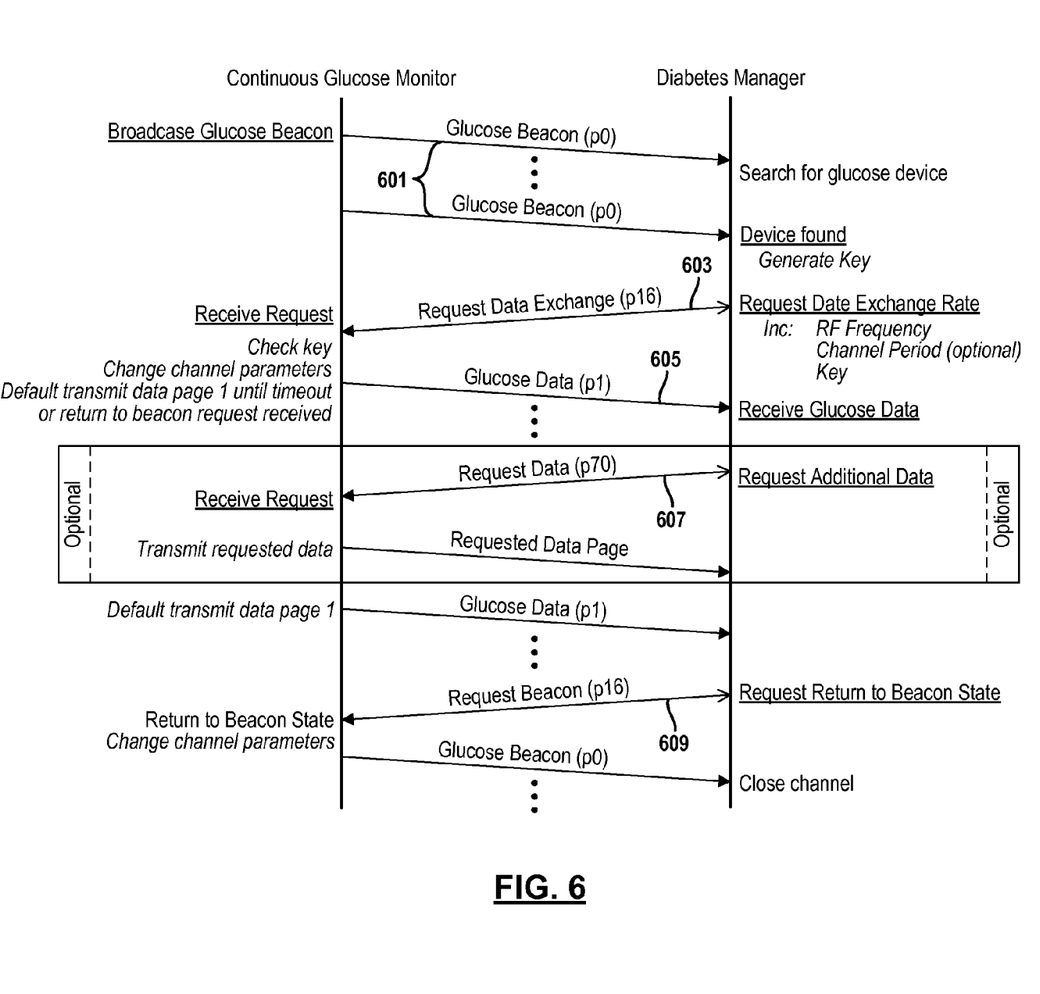
FIG. 6 is a diagram of a typical message flow in accordance with the ANT+ communication protocol.

FIG. 6 illustrates a typical message flow between a CGM 200 and a diabetes manager 104. In the beacon state, the CGM 200 will transmit a beacon every channel period (e.g., five minutes) as indicated at 601. The beacon message may be formatted, for example, in accordance with data page 0 set forth in the ANT+ Glucose Device Profile standard. It is noted that lines with a single arrow signifies a broadcast message; whereas, lines with an open and closed arrow at opposing ends signifies an acknowledgement message.

Upon receipt of the beacon, the diabetes manager 104 may send a data request to the CGM 200 as indicated at 603. The request to exchange data may be formatted, for example, in accordance with data page 16 as set forth in the ANT+ Glucose Device Profile standard. In response thereto, the CGM 200 will transition from a beacon state to a data exchange state. In some embodiments, the CGM 200 consumes electrical power at a lower rate in the beacon state than when operating in the data exchange rate. Once in the data exchange state, the CGM 200 can transmit blood glucose measures to the diabetes manager 104 as indicated at 605. The blood glucose measures may be formatted, for example, in accordance with data page 1 as set forth in the ANT+ Glucose Device Profile standard. During the data exchange state, additional information may be requested at 607 from the CGM 200 by the diabetes manager 104, for example using data page 70 as set forth in the ANT+ Glucose Device Profile standard.

Upon completing the data exchange, the diabetes manager will send a request to return to the beacon state to the CGM 200 as indicated at 609. In response thereto, the CGM 200 will transition from the data exchange state back to the beacon state. When returning to the beacon state, the CGM 200 will return to its default RF channel frequency and channel period for subsequent transmissions.

The CGM 200 may be configured to transmit blood glucose measures periodically to the diabetes manager 104. An error may occur during transmission, such that data packets are lost or otherwise not received by the diabetes manager 104. It is preferable that the CGM 200 continue to communicate with the diabetes manager in the standard data transfer mode, for example of the ANT communication protocol. Accordingly, improvements to the communication protocol are set forth below for recovering data from the CGM 200.

Figure 7:
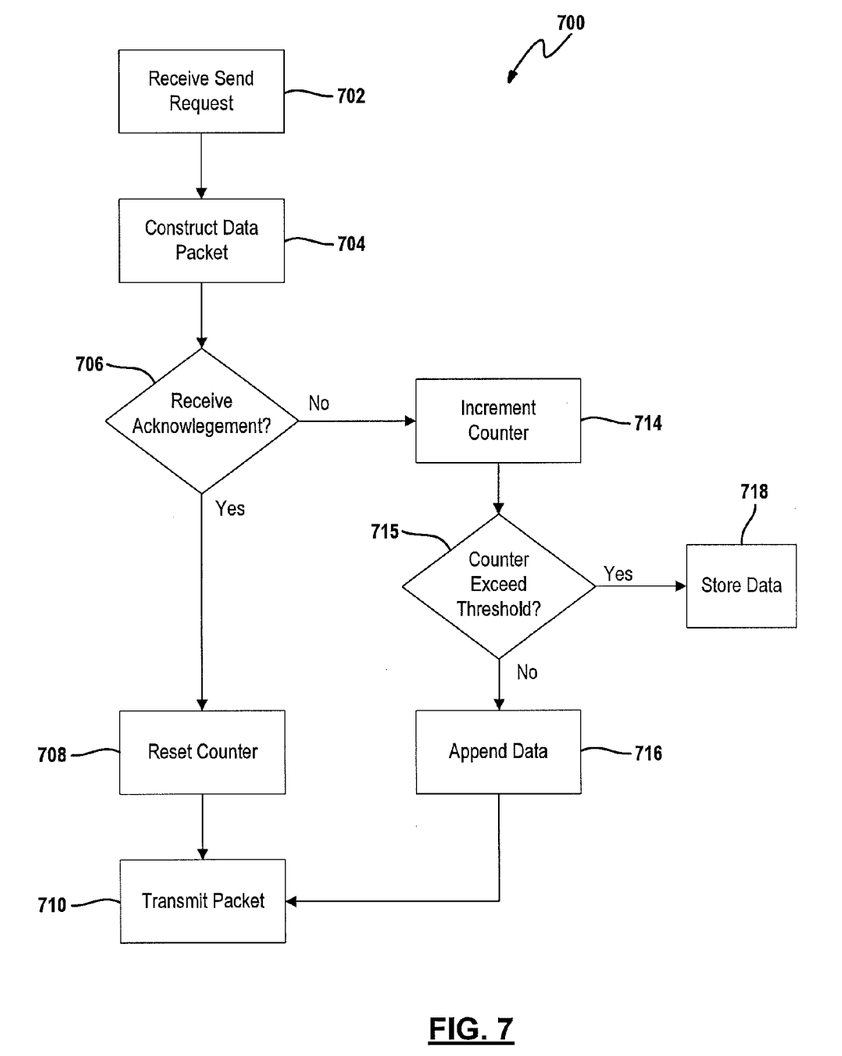
FIG. 7 is a flowchart depicting an exemplary technique for recovering lost data from the CGM.

FIG. 7 depicts an exemplary technique 700 for recovering data from the CGM 200. Upon receipt of a request to send data at 702 from the diabetes manager 104, the CGM transitions from a beacon state to a data exchange state as described above in relation to FIG. 6. In the data exchange state, the CGM operates at 704 to construct a data packet for transmission to the diabetes manager 104. The data packet generally include the blood glucose measures taken by the CGM 200 during the time interval since a data packet was last sent to the diabetes manager 104. As noted above, the blood glucose measures may be formatted, for example, in accordance with data page 1 as set forth in the ANT+ Glucose Device Profile standard.

Data packets sent by the CGM 200 can expect to receive an acknowledgement that the data packets were received by the diabetes manager 104. In the exemplary embodiment, the CGM 200 receives a request to enter a beacon state from the diabetes manager 104 as discussed above in relation to FIG. 6. In this embodiment, the request to enter a beacon state can serve as the acknowledgement that the recently sent data packets were received by the diabetes manager 104. Conversely, failure to receive the request to enter a beacon state within a predefined duration indicates that the data packets were not received by the diabetes manager. In an alternative embodiment, an acknowledge message is sent by the diabetes manager whether the data packets were or were not receive by the diabetes manager. Other types of acknowledgement mechanisms are also contemplated by this disclosure.

When an acknowledgment message was received from the most recently sent data packet, the CGM 200 transmits the newly constructed data packet at 710. Prior to transmitting the data packet, the CGM 200 further operates to reset a counter at 708, where the counter maintains a count of data packets that were sent by the CGM 200 but not received by the diabetes manager 104. Because the acknowledgement was received, it can be assumed that previously sent blood glucose measures were received by the diabetes manager 104. In an exemplary embodiment, blood glucose measures from previously sent data packets are stored locally in memory by the CGM 200 until the counter is reset. Once the counter is reset, the stored blood glucose measures may be erased from memory.

Conversely, when an acknowledgement for the most recently sent data packet was not received, the counter is incremented by one at 714. In one embodiment, the CGM 200 initiates a timer upon transmitting a data packet to the diabetes manager 104. The transmitted data packet is assumed to be lost or otherwise not received by the diabetes manager when the timer expires without the CGM 200 having received the request to enter a beacon state from the diabetes manager 104. The counter is then compared at 715 to a predefined limit (e.g., three). It is understood that the predefined limit may vary and is chosen based on the allowed packet size and/or data rates that optimize data transfer within a beacon period.

When the counter is less than or equal to the limit, the CGM 200 appends blood glucose measures from the lost data packet(s) at 716 to the newly constructed data packet. In this way, the CGM 200 may append blood glucose measures from one or more lost data packets up to the predefined limit such that the appended data fits within a data packet sized in accordance with the communication protocol. The newly constructed data packet is then transmitted at 710 by the CGM 200. In this way, blood glucose measures may be recovered from the CGM 200 while continuing to operate in the standard transfer mode. When the counter value exceeds a threshold, the CGM 200 stores the blood glucose measures from the lost data packets in a non-volatile memory for later retrieval as indicated at 718. In the exemplary embodiment, the diabetes manager 104 initiates a file transfer mode to retrieve the data from the lost data packets as further described below. In the context of other types of communication protocols, the CGM 200 may initiate a file transfer mode to transmit the data from the lost data packets to the diabetes manager 104. In any case, once the data packet has been sent, the CGM 200 returns to a beacon state and awaits the next request from the diabetes manager 104.

Figure 8:
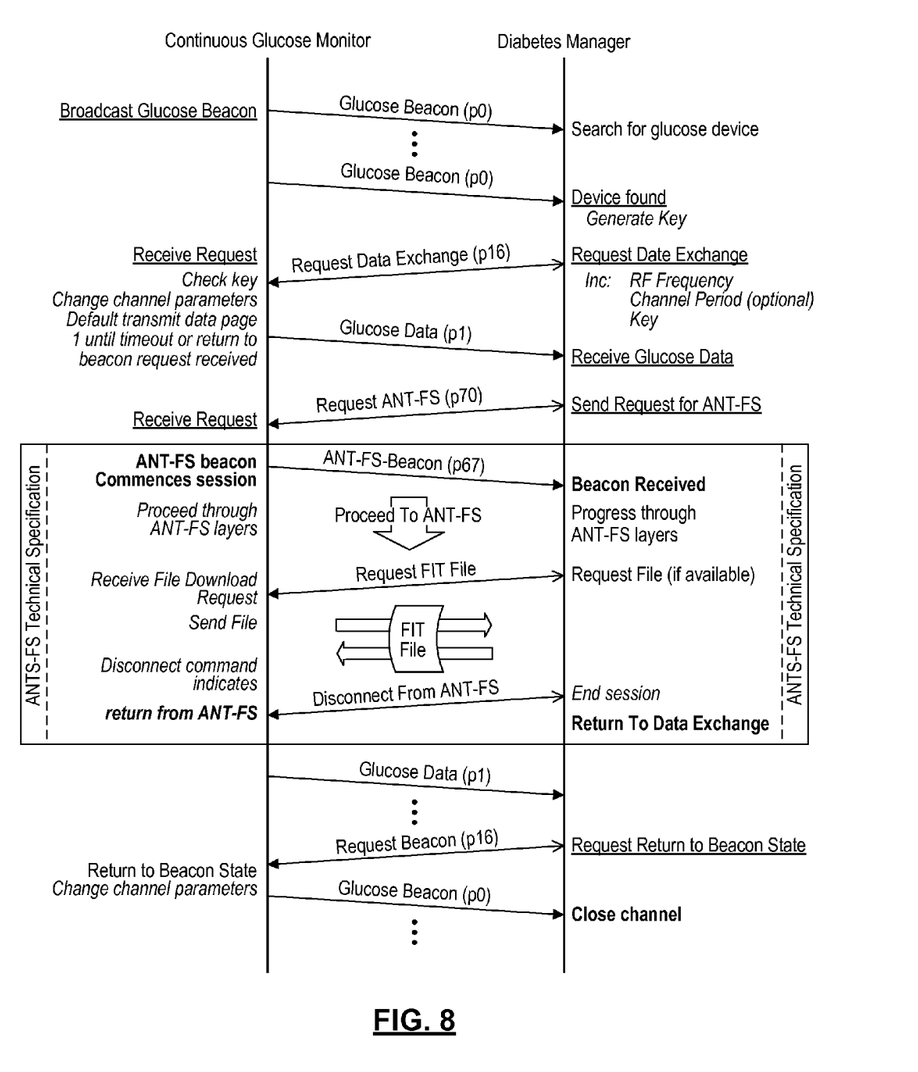
FIG. 8 is a diagram of a message flow transitioning from a standard transfer mode to a file share mode in accordance with the ANT+ communication protocol.

Communication between the CGM 200 and the diabetes manager 104 may transition from a standard transfer mode to a file share mode which supports larger packet sizes and higher data transfer rates as shown in FIG. 8. The ANT communication protocol supports a file share mode which is referred to as ANT-FS. In the exemplary embodiment, the CGM 200 and the diabetes manager 104 are both configured to support the ANT-FS protocol. The file share or file storage mode allows for larger amounts of data segments to be stored locally by the slave device and transferred subsequently to the master device. The transferred data segments can be a standard file format structure, a database structure or a compressed file structure. Moreover, the data transfer will occur at a higher data rate than data sent in the standard transfer mode. Further details for ANT-FS protocol may be found in the ANT File Share Technical Specification document although the concepts described herein may be extended to other types of file transfer protocols which typically transfer data at a higher data rate than the underlying communication protocol.

Figure 9:
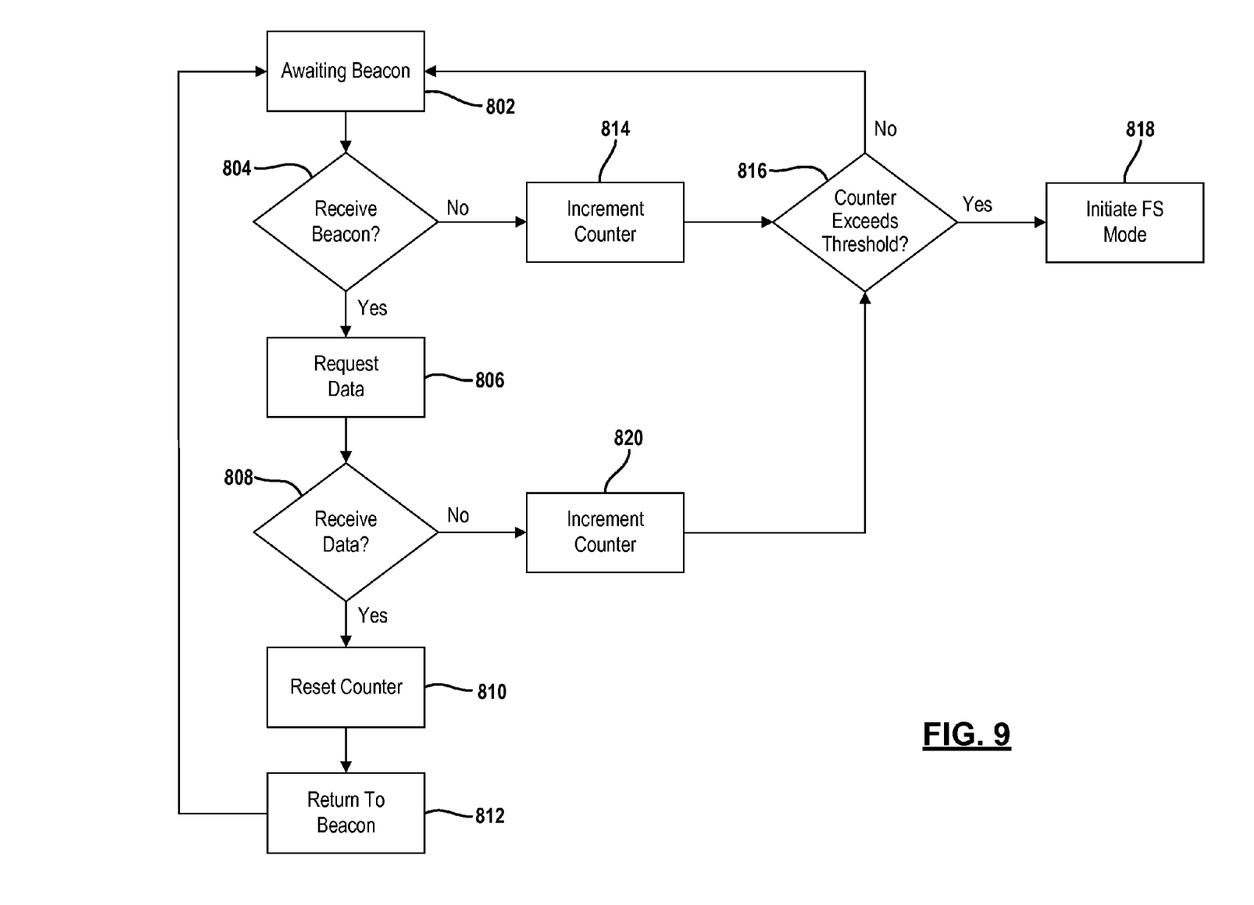
FIG. 9 is a flowchart depicting an exemplary technique for initiating a file sharing mode by the diabetes manager.

In context of the ANT communication protocol, the master device (i.e., the diabetes manager 104) initiates the file transfer mode as further described in relation to FIG. 9. During operation, the diabetes manager 104 awaits a beacon message from the CGM 200. In the exemplary embodiment, a beacon message is sent at predefined intervals (e.g., every five minutes) by the CGM 200. Once a communication session has been established between the CGM 200 and the diabetes manager 104, the diabetes manager 104 can expect to receive a beacon message at the defined interval. Missed beacon messages can be tracked by the diabetes manager 104. For example, when a beacon message is not received by the diabetes manager 104 at the expected time, the diabetes manager 104 can increment a counter which maintains a count of data packets not received by the diabetes manager 104 as indicated at 814. Likewise, when a request for blood glucose measures is sent by the CGM as indicated at 806 but the requested data is not received within the beacon period, the diabetes manager 104 increments the counter at 820. In this way, the diabetes manager 104 monitors the number of data packets expected but not received by the CGM.

The diabetes manager 104 may initiate the file transfer mode at any time while in the data exchange state. When the counter value exceeds a threshold, the diabetes manager 104 initiates a file transfer mode as indicated at 818. Specifically, the diabetes manager 104 sends a request to the CGM 200. The request message may be formatted, for example, in accordance with data page 70 set forth in the ANT+ Glucose Device Profile standard. Upon receiving the request, the CGM 200 will transmit a file sharing beacon, thereby transitioning from the data exchange state to a file sharing session. Once a file sharing session has begun, blood glucose measures from lost data packets may be sent from the CGM 200 to the diabetes manager 104 in accordance with the ANT-FS protocol. Upon completing the file sharing session, the diabetes manager 104 resets its lost packet counter and sends a disconnect command to the CGM 200 which in turn returns to the data exchange state.

When the data requested is successfully received by the diabetes manager 104, the diabetes manager 104 resets the counter at 810 and returns to a beacon state at 812. In the beacon state, the diabetes manager 104 awaits a beacon message from the CGM 200 as indicated at 802.

Figure 10:
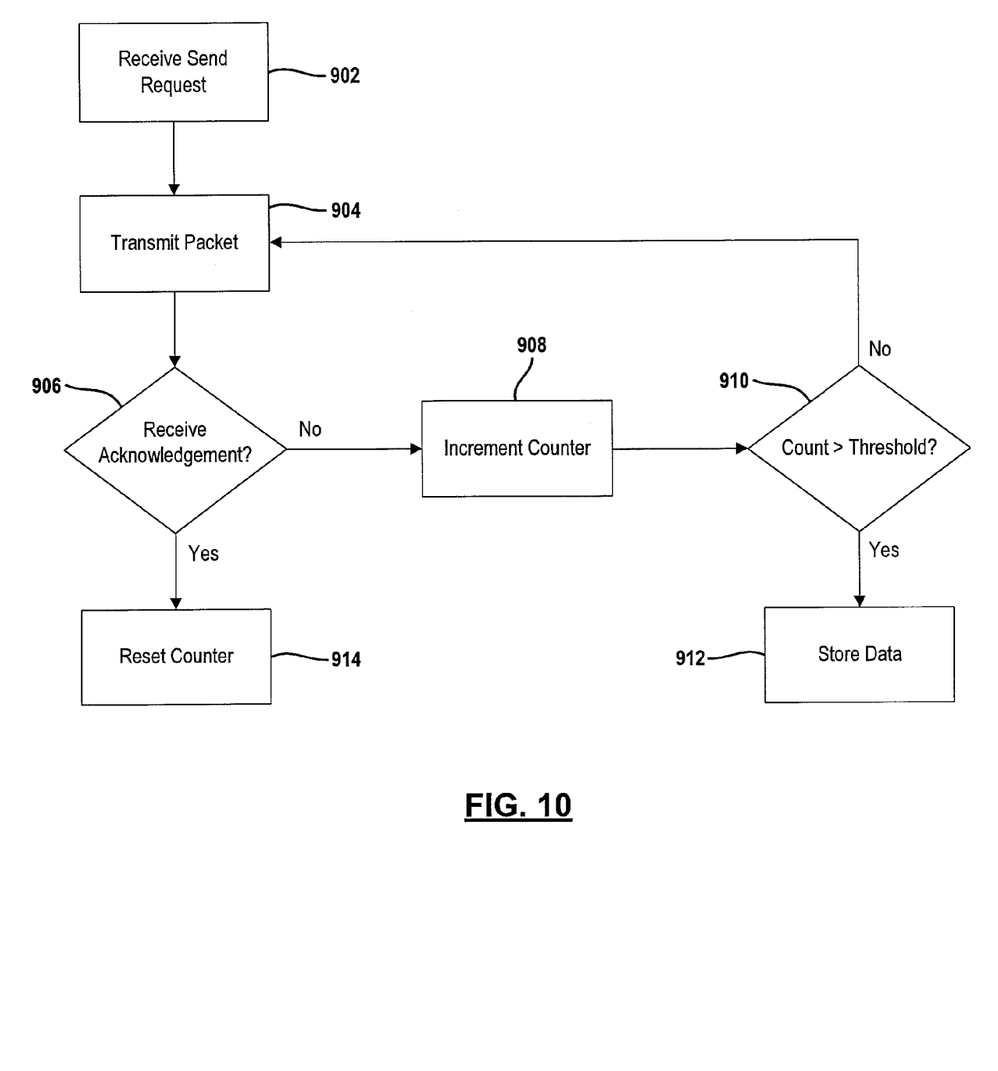
FIG. 10 is a flowchart depicting an alternative technique for recovering lost data from the CGM.

FIG. 10 depicts an alternative technique for recovering lost data from the CGM 200. Upon receipt of a request to send data at 902 from the diabetes manager 104, the CGM operates at 904 to transmit a data packet to the diabetes manager 104. The data packet generally include the blood glucose measures taken by the CGM 200 during the time interval since a data packet was last sent to the diabetes manager 104 and may be formatted, for example, in accordance with data page 1 as set forth in the ANT+ Glucose Device Profile standard.

For data packets sent, the CGM 200 can expect to receive an acknowledgement that the data packets were received by the diabetes manager 104. In the exemplary embodiment, the CGM 200 receives a request to enter a beacon state from the diabetes manager 104 as discussed above in relation to FIG. 6. Thus, the request to enter a beacon state serves as the acknowledgement that the recently sent data packet was received by the diabetes manager 104. Conversely, failure to receive the request to enter a beacon state within a predefined duration indicates that the data packet was not received by the diabetes manager.

When an acknowledgement was not received for the most recently sent data packet, a counter is incremented by one at 908, where the counter maintains a count of retransmission attempts by the CGM 200. Next, the value of the counter is compared at 910 to a predefined limit (e.g., three). The CGM 200 will attempt to retransmit the data packet when the counter value is less than the predefined limit as indicated at 904. That is, the CGM attempts to retransmit the lost data packet during the current beacon period. The process can be repeated until the counter value exceeds the predefined limit. The predefined limit may vary and is chosen to ensure retransmission attempts occur during the current beacon period. If retransmission attempts are unsuccessful and the counter value reaches the predefined limit, the blood glucose measures are stored locally in memory by the CGM 200 for subsequent transmission. On the other hand, when an acknowledgement is received for the most recently sent data packet, the counter is reset at 914. In response to the acknowledgement, the CGM 200 also returns to a beacon state. In this way, blood glucose measures may be recovered from the CGM 200 while continuing to operate in the standard transfer mode.

Concurrently, the diabetes manager 104 can monitor the number of expected data packets that were not received across multiple beacon periods as discussed in relation to FIG. 8. Accordingly, the diabetes manager 104 can initiate a file sharing mode when the number of expected but not received data packets exceeds a predefined threshold.

In a variant of this technique, blood glucose measures unsuccessfully transmitted in one beacon period may be transmitted in a subsequent beacon period by the CGM 200. Upon receiving a request to send data from the diabetes manager 104, the CGM 200 can determine whether the counter value is greater than zero, thereby indicating an unsuccessful transmission during one or earlier beacon periods. When the counter value is greater than zero, blood glucose measures from the earlier beacon periods may be appended to the current data packet in a similar manner as described in relation to FIG. 7. In this way, blood glucose measures may be recovered from the CGM 200 while continuing to operate in the standard transfer mode.

The techniques described herein can be implemented by one or more computer programs or applications executed by one or more processors. The computer programs and applications can include processor-executable instructions that are stored on a non-transitory tangible computer readable medium. The computer programs can also include stored data. Non-limiting examples of the non-transitory tangible computer readable medium are nonvolatile memory, magnetic storage, and optical storage.

As used herein, the term module can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module can include memory (shared, dedicated, or group) that stores code executed by the processor.

The term code, as used above, can include software, firmware, and/or microcode, and can refer to programs, routines, functions, classes, and/or objects. The term shared, as used above, means that some or all code from multiple modules can be executed using a single (shared) processor. In addition, some or all code from multiple modules can be stored by a single (shared) memory. The term group, as used above, means that some or all code from a single module can be executed using a group of processors. In addition, some or all code from a single module can be stored using a group of memories.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A computer-implemented method for communicating data between a continuous glucose monitor and a handheld diabetes manager, comprising:
constructing, by a continuous glucose monitor, a data packet for transmission during a current time interval in a series of sequential time intervals, where the data packet includes blood glucose measures taken by the continuous glucose monitor during the current time interval;
resetting, by the continuous glucose monitor, a counter upon receiving an acknowledgement of receipt of a data packet transmitted during the preceding time interval;
incrementing, by the continuous glucose monitor, the counter upon failing to receive an acknowledgement of receipt of a data packet transmitting during a time interval preceding the current time interval;
appending, by the continuous glucose monitor, blood glucose measures taken by the continuous glucose measure during the preceding time interval to the data packet when the counter is less than a threshold;
transmitting, by the continuous glucose monitor, the data packet at a first data rate via a wireless data link to the handheld diabetes manager when the counter is less than the threshold;
storing, by the continuous glucose monitor, blood glucose measures taken by the continuous glucose monitor during the current time interval and the preceding time interval in a non-volatile memory, when the counter is equal to or exceeds the threshold and upon failing to receive an acknowledgement of receipt of a data packet transmitting; and
subsequent to storing the blood glucose measures in the non-volatile memory, transmitting, by the continuous glucose monitor, the blood glucose measures stored in the non-volatile memory at a second data rate higher than the first data rate.

2. The method of claim 1 further comprises further comprises receiving, by the continuous glucose monitor, a request to send data from the handheld diabetes manager, and transmitting, by the continuous glucose monitor, the data packet in response to the request to send data.

3. The method of claim 1 further comprises periodically sending, by the continuous glucose monitor, a beacon to the handheld diabetes manager, where the beacon includes data pertaining to an operating state of the continuous glucose monitor; and receiving, by the continuous glucose monitor, a request to send data from the handheld diabetes manager in response to the beacon.

4. The method of claim 3 further comprises transitioning, by the continuous glucose monitor, to a data exchange state from a beacon state in response to the request to send data, where the continuous glucose monitor operates in the data exchange state to consume electrical power at a higher rate than in the beacon state.

5. The method of claim 4 further comprises:
initiating, by the continuous glucose monitor, a timer having a predefined duration in response to the transmission of a data packet during the preceding time interval; and
appending, by the continuous glucose monitor, blood glucose measures taken by the continuous glucose monitor during the preceding time interval, upon expiration of the timer without receipt of a request to enter a beacon state from the handheld diabetes manager.

6. The method of claim 1 further comprises transmitting the data packet in accordance with ANT+ communication protocol.

7. The method of claim 1 further comprises receiving, by the continuous glucose monitor, a request to enter a file sharing mode from the handheld diabetes manager, and initiating a file sharing mode in response to the request to enter a file sharing mode.

8. The method of claim 7 further comprises monitoring, by the handheld diabetes manager, data packets received from the continuous glucose monitor, and sending, by the handheld diabetes manager, the request to enter a file sharing mode when the data packets expected but not received from the continuous glucose monitor exceeds a limit.

9. The method of claim 7 further comprises transmitting the blood glucose measures in the non-volatile memory in accordance with ANT-FS protocol.

10. A computer-implemented method for communicating data between a continuous glucose monitor and a handheld diabetes manager, comprising:
receiving, by the continuous glucose monitor, a request to send data from the handheld diabetes manager;
constructing, by the continuous glucose monitor, a data packet in response to the request to send data, the data packet includes blood glucose measures taken by the continuous glucose monitor during a first time interval;
appending, by the continuous glucose monitor, blood glucose measures to the data packet upon failing to receive an acknowledgement of receipt from the handheld diabetes manager, the blood glucose measures taken by the continuous glucose measure during a time interval preceding the first time interval;
transmitting, by the continuous glucose monitor, the data packet via a wireless data link to the handheld diabetes manager in accordance with ANT communication protocol;
receiving, by the continuous glucose monitor, a request to enter a file sharing mode from the handheld diabetes manager, where the request to enter a file sharing mode is sent by the handheld diabetes manager when data packets expected but not received from the continuous glucose monitor exceeds a threshold; and
sending, by the continuous glucose monitor, blood glucose measures to the handheld diabetes manager in response to the request to enter a file sharing mode, the blood glucose measures sent in accordance with the ANT-FS protocol.

11. The method of claim 10 further comprises periodically sending, by the continuous glucose monitor, a beacon to the handheld diabetes manager, where the beacon includes data pertaining to an operating state of the continuous glucose monitor; and receiving, by the continuous glucose monitor, the request to send data in response to the beacon.

12. The method of claim 11 further comprises transitioning, by the continuous glucose monitor, to a data exchange state from a beacon state in response to the request to send data, where the continuous glucose monitor operates in the beacon state to consume electrical power at a lower rate than in the data exchange state.

13. The method of claim 11 further comprises transitioning, by the continuous glucose monitor, to the beacon state from the data exchange state in response to a request to enter a beacon state received from the handheld diabetes manager, where the request to enter a beacon state serves as the acknowledgement.

14. A computer-implemented method for communicating data between a continuous glucose monitor and a handheld diabetes manager, comprising:
transmitting, by the continuous glucose monitor, a first data packet via a wireless data link to the handheld data manager during a first time interval in a series of sequential time intervals, wherein the first data packet includes blood glucose measures taken by the continuous glucose monitor prior to the first time interval and is transmitted in accordance with the ANT communication protocol;
receiving, by the continuous glucose monitor, an acknowledgement regarding the transmission of the first data packet;
retransmitting, by the continuous glucose monitor, the first data packet via the wireless data link to the handheld diabetes manager during the first time interval when the acknowledgement indicates an unsuccessful transmission of the first data packet;
receiving, by the continuous glucose monitor, an acknowledgement regarding the retransmission of the first data packet; and
transmitting, by the continuous glucose monitor, a second data packet via the wireless data link during a second time interval in the series of time intervals, wherein the second data packet includes blood glucose measures taken by the continuous glucose monitor during the first time interval and further includes blood glucose measures taken by the continuous glucose measure prior to the first time interval only when the acknowledgement indicates an unsuccessful retransmission of the first data packet.

15. The method of claim 14 further comprises periodically sending, by the continuous glucose monitor, a beacon to the handheld diabetes manager, where the beacon includes data pertaining to an operating state of the continuous glucose monitor; and receiving, by the continuous glucose monitor, a request to send data from the handheld diabetes manager.

16. The method of claim 15 further comprises transitioning, by the continuous glucose monitor, to a data exchange state from a beacon state in response to the request to send data, where the continuous glucose monitor operates to consume electrical power at a lower rate in the beacon state than in the data exchange state.

17. The method of claim 15 further comprises transmitting, by the continuous glucose monitor, the first data packet in response to the request to send data.

18. The method of claim 15 further comprises transitioning, by the continuous glucose monitor, to the beacon state from the data exchange state in response to a request to enter a beacon state received from the handheld diabetes manager.

19. The method of claim 14 further comprises receiving, by the continuous glucose monitor, a request to enter a file sharing mode from the handheld diabetes manager, and initiating a file sharing mode in response to the request to enter a file sharing mode.

20. The method of claim 19 further comprises monitoring, by the handheld diabetes manager, data packets received from the continuous glucose monitor, and sending, by the handheld diabetes manager, the request to enter a file sharing mode when the data packets expected but not received from the continuous glucose monitor exceeds a threshold.

21. The method of claim 19 further comprises sending, by the continuous glucose monitor, blood glucose measures to the handheld diabetes manager in accordance with the ANT-FS protocol.

\* \* \* \* \*

UNITED STATES PATENT AND TRADEMARK OFFICE
CERTIFICATE OF CORRECTION

PATENT NO. : 9,226,702 B2  
APPLICATION NO. : 13/650160  
DATED : January 5, 2016  
INVENTOR(S) : Clint A. Ecoff et al.

Page 1 of 1

It is certified that error appears in the above-identified patent and that said Letters Patent is hereby corrected as shown below:

Title Page  
Item (71) Applicant, line 1,   "Roche Diagnostics Operations, Inc." should be --Roche Diabetes Care, Inc.--

In The Specification  
Column 5  
Line 67   "Continual®" should be --Continua®--

In The Claims  
Column 12  
Lines 59-60   delete "further comprises" ($2^{nd}$ occurrence)

Signed and Sealed this  
Twenty-fourth Day of May, 2016

Michelle K. Lee  
*Director of the United States Patent and Trademark Office*